United States Patent
Powers et al.

(10) Patent No.: US 9,304,123 B2
(45) Date of Patent: Apr. 5, 2016

(54) BIOMARKERS USED TO DETECT AND MONITOR NEUROLOGICAL AUTOIMMUNE DISEASES

(71) Applicant: NUtech Ventures, Lincoln, NE (US)

(72) Inventors: Robert Powers, Lincoln, NE (US); Jay Reddy, Lincoln, NE (US); Teklab Gebregiworgis, Lincoln, NE (US); Chandirasegaran Massilamany, Lincoln, NE (US); Arunakumar Gangaplara, Lincoln, NE (US); Zsolt Illes, Odense SV (DK)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 13/962,571

(22) Filed: Aug. 8, 2013

(65) Prior Publication Data

US 2014/0045197 A1 Feb. 13, 2014

Related U.S. Application Data

(60) Provisional application No. 61/680,938, filed on Aug. 8, 2012.

(51) Int. Cl.
*G01N 33/493* (2006.01)
*G01N 33/564* (2006.01)
*G01N 33/53* (2006.01)

(52) U.S. Cl.
CPC .......... *G01N 33/493* (2013.01); *G01N 33/5308* (2013.01); *G01N 33/564* (2013.01); *G01N 2500/10* (2013.01); *G01N 2800/285* (2013.01); *G01N 2800/50* (2013.01)

(58) Field of Classification Search
CPC .................................................... G01N 33/493
See application file for complete search history.

(56) References Cited

PUBLICATIONS

Behan et al., The sad plight of multiple sclerosis research (low on fact, high on fiction): critical data to support it being a neurocristopathy, Dec. 2010, Inflammopharmacol 18(6):265-290.*
Upton, A., Concerning: "The sad plight of multiple sclerosis research (low on fact, high on fiction): critical data to support it being a neurocristopathy" by Peter O. Behan and Abhijit Chaudhuri, Dec. 2010, Inflammopharmacol 18(6):263.*
Ransohoff, R., Animal models of multiple sclerosis: the good, the bad and the bottom line, Aug. 2012, Nature Neourscience 15(8):1074-1077.*
Banwell et al., "Multiple Sclerosis in Children: Clinical Diagnosis, Therapeutic Strategies, and Future Directions," *Lancet Neurol*, Oct. 2007, 6:887-902.
Chiba et al., "Fingolimod (FTY720), Sphingosine 1-Phosphate Receptor Modulator, Shows Superior Efficacy As Compared With Interferon-β in Mouse Experimental Autoimmune Encephalomyelitis," *Int Immunopharmacol*, 2011, 11:366-372.
Choi et al., "FTY720 (fingolimod) Efficacy in an Animal Model of Multiple Sclerosis Requires Astrocyte Sphingosine 1-Phosphate Receptor 1 (S1P1) Modulation," *Proc Natl Acad Sci USA*, Jan. 11, 2011, 108(2):751-756.
Csepany, "[Current treatment of multiple sclerosis]," *Lege Artis Med*, Feb. 2011, 21:97-104 (English Abstract).
Esbjerg et al., "Reporting Delay and Corrected Incidence of Multiple Sclerosis," *Stat in Med*, 1999, 18:1691-1706.
Fadil et al., "Differential Diagnosis of Multiple Sclerosis," *Int Rev Neurobiol*, 2007, 79:393-422.
Forgue et al., "NMR Metabolic Profiling of *Aspergillus nidulans* to Monitor Drug and Protein Activity," *Journal of Proteome Research*, 2006, 5:1916-1923.
Giesser, "Diagnosis of Multiple Sclerosis," *Neurol Clin*, 2011, 29:381-388.
Giovannoni, "Promising Emerging Therapies for Multiple Sclerosis," *Neurol Clin*, 2011, 29:435-448.
Glabinski et al., "[13] Murine Experimental Autoimmune Encephalomyelitis: A Model of Immune-Mediated Inflammation and Multiple Sclerosis," *Methods Enzymol.*, 1997, 288:182-190.
Gold et al., "Understanding Pathogenesis and Therapy of Multiple Sclerosis Via Animal Models: 70 Years of Merits and Culprits in Experimental Autoimmune Encephalomyelitis Research," *Brain*, 2006, 129:1953-1971.
Hahn et al., "Differential Diagnosis and Evaluation in Pediatric Multiple Sclerosis," *Neurology*, 2007, 68(2):513-22.
Halouska and Powers, "Negative impact of noise on the principal component analysis of NMR data," *Journal of Magnetic Resonance*, 2006, 178:88-95.
Halouska et al., "Use of NMR Metabolomics to Analyze the Targets of D-Cycloserine in Mycobacteria: Role of $_D$-Alanine Racemase," *Journal of Proteome Research*, 2007, 6:4608-4614.
Harris and Sadiq, "Disease Biomarkers in Multiple Sclerosis: Potential for Use in Therapeutic Decision Making," *Mol. Diagn. Ther.*, 2009, 13(4):225-244.
Kataoka et al., "FTY720, Sphingosine 1-Phosphate Receptor Modulator, Ameliorates Experimental Autoimmune Encephalomyelitis by Inhibition of T Cell Infiltration," *Cell Mol Immunol*, Dec. 2005, 2(6):439-448.
Kerlero de Rosbo et al., "Reactivity to Myelin Antigens in Multiple Sclerosis: Peripheral Blood Lymphocytes Respond Predominantly to Myelin Oligodendrocyte Glycoprotein," *J Clin Invest*, Dec. 1993, 92:2602-2608.
Kolker et al., "3-Ureidopropionate Contributes to the Neuropathology of 3-Ureidopropionase Deficiency and Severe Propionic Aciduria: A Hypothesis," *Journal of Neuroscience Research*, 2001, 66:666-673.
Lee et al., "Proinflammatory T-Cell Responses to Gut Microbiota Promote Experimental Autoimmune Encephalomyelitis" *Proceedings of the National Academy of Sciences*, Mar. 15, 2011, 108(1):4615-4622.
Lourenco et al., "Proteomics-Based Technologies in the Discovery of Biomarkers for Multiple Sclerosis in the Cerebrospinal Fluid," *Curr. Mol. Med.*, 2011, 11:326-349.

(Continued)

*Primary Examiner* — John Ulm
(74) *Attorney, Agent, or Firm* — Fish & Richardson P.C.

(57) ABSTRACT

Biomarkers of neurological autoimmune diseases are described, and methods of using such biomarkers also are described.

12 Claims, 12 Drawing Sheets

(56) References Cited

PUBLICATIONS

Lutton et al., "Multiple Sclerosis: Etiological Mechanisms and Future Directions," *Exp Biol Med*, 2004, 229:12-20.

Marne et al., "Changes in the Ascertainment of Multiple Sclerosis," *Neurology*, Oct. 2005, 65:1066-1070.

Marne et al., "Comorbidity Delays Diagnosis and Increases Disability At Diagnosis In Ms," *Neurology*, Jan. 13, 2009, 72:117-124.

Massilamany et al., "Detection of Autoreactive CD4 T Cells Using Major Histocompatibility Complex Class II Dextramers," *BMC Immunol*, 2011, 12:40-53.

Massilamany et al., "An Epitope From *Acanthamoeba castellanii* That Cross-React With Proteolipid Protein 139-151-Reactive T Cells Induces Autoimmune Encephalomyelitis in SJL Mice," *J Neuroimmunol*, 2010, 219:17-24.

Massilamany et al., "Gender Differences in CNS Autoimmunity Induced by Mimicry Epitope for PLP 139-151 in SJL Mice," *J Neuroimmunol*, 2011, 230:95-104.

McDonald et al., "Recommended Diagnostic Criteria for Multiple Sclerosis: Guidelines From the International Panel on the Diagnosis of Multiple Sclerosis" *Ann Neurol*, 2001, 50:121-127.

Mendel et al., "A Myelin Oligodendrocyte Glycoprotein Peptide Induces Typical Chronic Experimental Autoimmune Encephalomyelitis in H2b Mice: Fine Specificity and T Cell Receptor V Beta Expression of Encephalitogenic T Cells," *Eur. J. Immunol.*, 1995, 25:1951-1959.

Miller, "The Importance of Early Diagnosis of Multiple Sclerosis," *J Manag Care Pharm*, Jun. 2004, 10:S4-11.

Miller et al., "Experimental Autoimmune Encephalomyelitis in the Mouse," *Curr. Prot. Immunol.*, May 2007, 26 pages.

Nath et al., "Metformin Attenuated the Autoimmune Disease of the Central Nervous System in Animal Models of Multiple Sclerosis," *J. Immunol*, Jun. 15, 2009, 182(12):8005-8014.

Neu et al., "Activation of $GABA_A$ Receptors by Guanidinoacetate: A Novel Pathophysiological Mechanism," *Neurobiology of Disease*, 2002, 11:298-307.

Noseworthy et al., " Multiple sclerosis," *N Engl J Med*, Sep. 28, 2000, 343:938-952.

Papadopoulos et al., "FTY720 Ameliorates MOG-Induced Experimental Autoimmune Encephalomyelitis by Suppressing Both Cellular and Humoral Immune Responses," *J Neurosci Res*, 2010, 88:346-359.

Polman et al., "Diagnostic Criteria for Multiple Sclerosis: 2005 Revisions to the 'McDonald Criteria'," *Ann Neurol*, 2005, 58:840-846.

Powers, "Advances in Nuclear Magnetic Resonance for Drug Discovery," *Expert Opin. Drug Discovery*, Oct. 1, 2009, 4(10):1077-1098.

Powers, "NMR Metabolomics and Drug Discovery," *Magnetic Resonance in Chemistry*, 2009, 47:S2-S11.

Rigotti et al., "Global N-Acetyl-aspartate Declines Even in Benign Multiple Sclerosis," *Am J Neuroradiol.*, Jan. 2011, 32(1):204-209.

Rolak and Fleming, "The Differential Diagnosis of Multiple Sclerosis," Neurologist, Mar. 2007, 13(2):57-72.

Sadykov et al., "Using NMR Metabolomics to Investigate Tricarboxylic Acid Cycle Dependent Signal Transduction in *Staphylococcus epidermidis*" *J. Biol. Chem.*, Nov. 19, 2010, 285(47):36616-36624.

Sadykov et al., "Tricarboxylic Acid Cycle Dependent Regulation of *Staphylococcus epidermidis* Polysaccharide Intercellular Adhesin Synthesis," *Journal of Bacteriology*, 2008, 190(23):7621-7632.

Sospedra and Martin, "Immunology of Multiple Sclerosis," *Annu Rev Immunol*, 2005, 23:683-747.

Sriram and Steiner, "Experimental allergic encephalomyelitis: A Misleading Model of Multiple Sclerosis," *Ann. Neurol.*, 2005, 58:939-945.

Steinman et al., "Virtues and pitfalls of EAE for the development of therapies for multiple sclerosis," *Trends Immunol.*, Nov. 11, 2005, 26(11):565-571.

Steinman and Zamvil, "How to Successfully Apply Animal Studies in Experimental Allergic Encephalomyelitis to Research on Multiple Sclerosis," *Ann. Neurol*, 2006, 60:12-21.

Webb et al., "Sphingosine 1-phosphate receptor agonists attenuate relapsing-remitting experimental autoimmune encephalitis in SJL mice," *J Neuroimmunol*, 2004, 153:108-121.

Werth et al., "Analysis of Metabolomic PCA Data using Tree Diagrams," *Analytical Biochemistry*, Apr. 1, 2010, 399(1):56-63.

Wikoff et al., "Metabolomics analysis reveals large effects of gut microflora on mammalian blood metabolites," *Proceedings of the National Academy of Sciences*, Mar. 10, 2009, 106(10):3698-3703.

Wishart et al., "HMDB: a knowledgebase for the human metabolome," *Nucleic Acids Research*, 2009, 37:D603-D610.

Zhang et al., "NMR Analysis of a Stress Response Metabolic Signaling Network," *Journal of Proteome Research*, Aug. 5, 2011, 10(8):3743-3754.

\* cited by examiner

BIOMARKERS USED TO DETECT AND MONITOR NEUROLOGICAL AUTOIMMUNE DISEASES

CROSS REFERENCE TO RELATED APPLICATIONS

This application claims the priority of benefit to U.S. application Ser. No. 61/680,938 filed on Aug. 8, 2012. The previous application is incorporated herein in its entirety.

FEDERALLY SPONSORED RESEARCH OR DEVELOPMENT

This invention was made with government support under Grant Nos. R21 AI081154, RR015468, and P20 RR017675 awarded by the National Institutes of Health. The government has certain rights in the invention.

TECHNICAL FIELD

This disclosure generally relates to biomarkers for neurological autoimmune diseases and methods of using such biomarkers.

BACKGROUND

Autoimmune diseases arise from an inappropriate immune response by the body against substances or tissues normally found in the body. Neurological autoimmune diseases are those autoimmune diseases that affect some aspect of the neurological system (e.g., the central nervous system or the peripheral nervous system). Biomarkers of one or more neurological autoimmune diseases, especially those biomarkers that can be evaluated non-invasively, are useful in the art.

SUMMARY

Biomarkers of neurological autoimmune diseases are provided, and methods of using such biomarkers also are provided.

In one aspect, a method of determining if a patient is suffering from, or is at risk of suffering from, a neurological autoimmune disease is provided. Such a method includes collecting a urine sample from a patient; and determining the levels of one or more biomarkers in the patient's urine, wherein the one or more biomarkers are selected from the group consisting of 3-ureidopropionic acid, guanidinoacetate and indoxyl sulfate. Generally, an increase in the level of the one or more biomarkers in the patient's urine is indicative of the presence of a neurological autoimmune disease in the patient. A representative neurological autoimmune disease is multiple sclerosis.

In some embodiments, the biomarkers are 3-ureidopropionic acid and guanidinoacetate. In some embodiments, the biomarkers are 3-ureidopropionic acid and indoxyl sulfate. In some embodiments, the biomarkers are guanidinoacetate and indoxyl sulfate. In some embodiments, the biomarkers are 3-ureidopropionic acid, guanidinoacetate and indoxyl sulfate. The levels of the one or more biomarkers can be determined, for example, using an immunoassay, chromatography, spectroscopy or NMR.

In some embodiments, the levels of the one or more biomarkers in the patient's urine are compared to the levels of the one or more biomarkers in a control patient that does not suffer from a neurological autoimmune disease. In some embodiments, the levels of the one or more biomarkers in the patient's urine are compared to a standardized control.

In another aspect, a method of determining whether a compound is effective for treating a subject having a neurological autoimmune disease is provided. Such a method typically includes collecting a first urine sample from a subject; determining the levels of one or more biomarkers in the first urine sample, wherein the one or more biomarkers are selected from the group consisting of 3-ureidopropionic acid, guanidinoacetate and indoxyl sulfate; administering a compound to the subject; collecting a second urine sample from the subject; and determining the levels of one or more of the biomarkers in the second urine sample. Generally, a decrease in the level of one or more biomarkers in the second urine sample relative to the first urine sample is indicative of a compound that is effective for treating a subject having a neurological autoimmune disease. In one embodiment, the neurological autoimmune disease is multiple sclerosis.

In some instances, the subject is a non-human animal. In some instances, the subject is a human.

In some embodiments, the biomarkers are 3-ureidopropionic acid and guanidinoacetate. In some embodiments, the biomarkers are 3-ureidopropionic acid and indoxyl sulfate. In some embodiments, the biomarkers are guanidinoacetate and indoxyl sulfate. In some embodiments, the biomarkers are 3-ureidopropionic acid, guanidinoacetate and indoxyl sulfate. The levels of the one or more biomarkers can be determined, for example, using an immunoassay, chromatography, spectroscopy or NMR.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A: Preliminary Experiments and Results

Part B: NMR Metabolomics-Based Analysis of Urine

Figure 3:
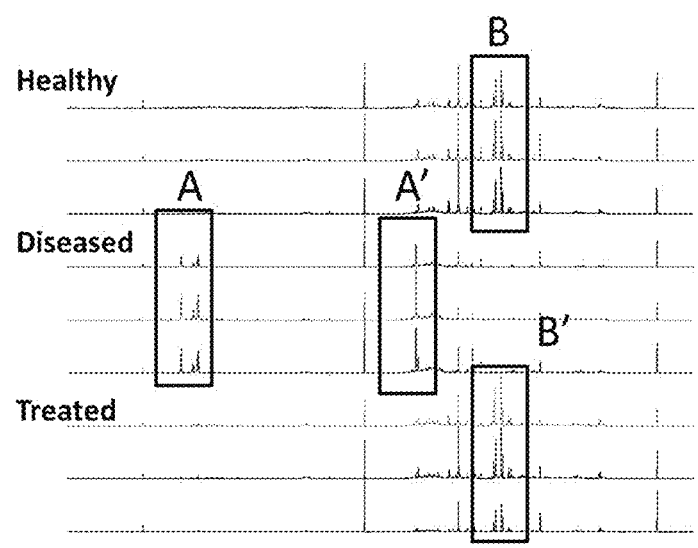

FIG. 3 is a graph showing the 1D $^1$H-NMR spectrum of healthy, diseased and treated mice.

Figure 4:
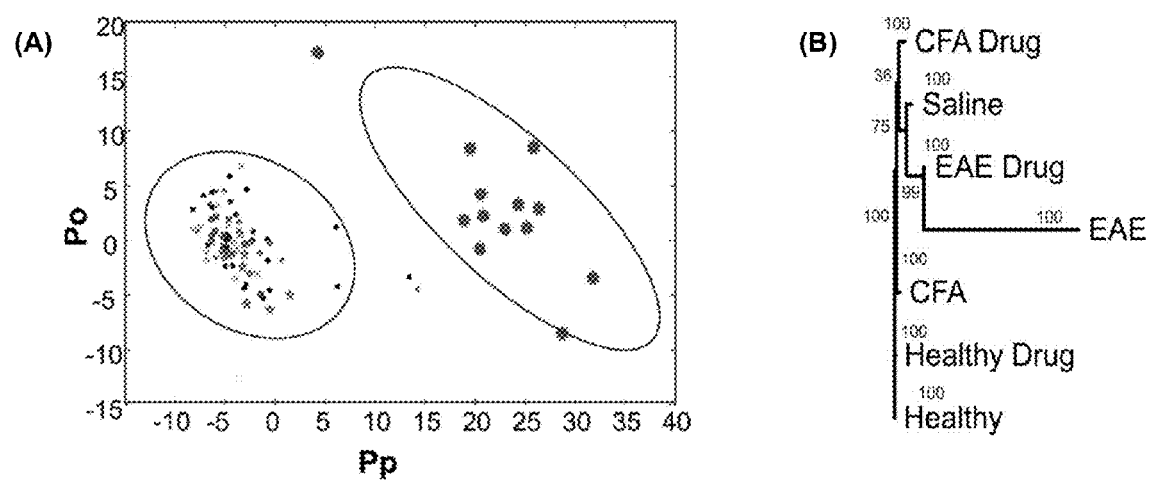

FIG. 4, Panel (A) is the 2D OPLS-DA score plot analysis of healthy (dark square), saline injected (5-point star), CFA injected (dark pentagon), diseased (large sun-shaped star), healthy treated with fingolimod (light square), CFA injected mice treated with fingolimod (light circle), and diseased mice treated with fingolimod (dark circle). Panel (B) is a metabolomics tree diagram based on the 2D OPLS-DA score plot of Panel (A).

Figure 5:
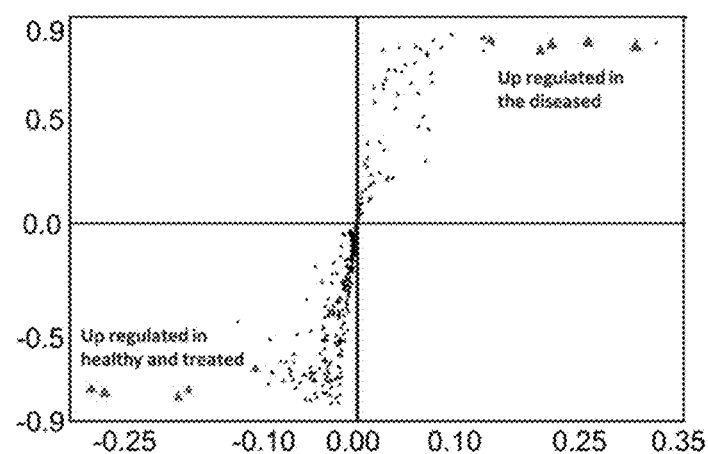

FIG. 5 is an OPLS-DA S-plot for urine collected from healthy, saline-injected, CFA-injected, EAE mice (diseased), healthy mice treated with Fingolimod, CFA-injected mice treated with Fingolimod, and diseased mice treated with Fingolimod.

Figure 6:
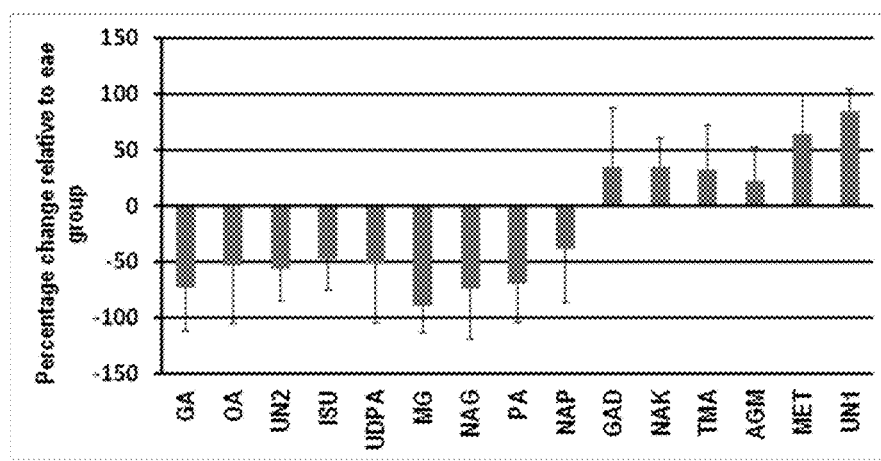

FIG. 6 is a bar graph of metabolites up- or down-regulated in the urine of EAE mice. GA (guanidoacetic acid), OA (oxoglutaric acid), UN2 (unknown_2), ISU (indoxylsulfate), UDPA (ureidopropionic acid), MG (methylguanidine), NGA (N-acetylglutamic acid), PA (pimelic acid), NAP (N-acetylputrescine), GAD (glyceraldehyde), NAK (N6-acetyllysine), TMA (trimethylamine), AGM (agmatine), MET (methionine), and UN1(unknown_1).

Like reference symbols in the various drawings indicate like elements.

DETAILED DESCRIPTION

Neurological autoimmune diseases such as multiple sclerosis (MS) are very challenging diseases to properly diagnose, and misdiagnosis is common. The diagnosis of MS typically uses the McDonald criteria (McDonald et al., 2001, *Ann. Neurol.*, 50:121-7; Polman et al., 2005, *Ann. Neurol.*, 58:840-6), which relies on history, magnetic resonance imaging, visual evoked potentials, cerebrospinal fluid analysis and hematology. Significant effort has been employed to identify biomarkers from cerebrospinal fluid (CSF) to facilitate a diagnosis for MS, but this endeavor has proven to be extremely challenging and has not been successful to date. Additionally, there are associated risks with obtaining CSF from patients. Therefore, a study was undertaken to investigate whether urine metabolites could be used as biomarkers of MS and to evaluate the in vivo activity of MS drugs, given that urine can be obtained non-invasively.

Three different metabolites were identified in urine, each of which can be used as a biomarker to detect or diagnose a neurological autoimmune disease such as MS in a patient suspected of suffering from such a disease, or at risk of suffering from such a disease. Similarly, any of the three biomarkers identified herein can be used to evaluate the effectiveness or efficacy of a compound (e.g., a drug) for treating such a disease.

One of the biomarkers, indoxyl sulfate (Human Metabolome Database (HMDB) 00682), is a dietary protein metabolite and also is a metabolite of the amino acid, tryptophan. In addition, indoxyl sulfate strongly decreases the levels of glutathione, which is one of the most active antioxidant systems of the cell. The other biomarkers, guanidinoacetate (HMDB 00128) and 3-ureidopropionic acid (HMDB 00026), are intermediates in the metabolism of amino acids and nucleic acids, respectively, and have been shown to be associated with neurological diseases (Kolker et al., 2001, *J. Neurosci. Res.*, 66:666-673; Neu et al., 2002, *Neurobiol. Dis.*, 11:298-307), but not necessarily neurological diseases with an autoimmune component. All three biomarkers are statistically significantly down-regulated in an animal model of suffering from a neurological autoimmune disease similar to MS.

Animals having an existing or induced disease or injury that is similar to a human condition are used routinely in research as animal models. Those skilled in the art would appreciate that rats, mice, guinea pigs, rabbits, and monkeys can be induced to exhibit Experimental Autoimmune Encephalomyelitis (EAE), which results in an animal model exhibiting an autoimmune disease characterized by inflammation and demyelination of the central nervous system (CNS) (Gold et al., 2006, *Brain*, 129:1953-71; Miller et al., 2007, *Curr. Prot. Immunol.*, Ch 15, Unit 15.1). EAE is considered to be an animal model of MS because it exhibits delayed onset; chronic-progressive course; relapsing-course; and widespread lesions. See, for example, Steinman et al., 2005, *Trends Immunol.*, 26:565-71; and Steinman & Zamvil, 2006, *Ann. Neurol.*, 60:12-21. While the methods described herein can be used in the diagnosis and evaluation of MS, the methods described herein also can be used in the diagnosis and evaluation of symptoms associated with other neurological autoimmune diseases.

Thus, determining the level of one or more of these biomakers in urine can be used to determine if a patient is suffering from or is at risk of suffering from a neurological autoimmune disease. As described herein, a decrease (e.g., a statistically significant decrease) in the level of one, two or three of the biomarkers (e.g., 3-ureidopropionic acid, guanidinoacetate, or indoxyl sulfate; 3-ureidopropionic acid & guanidinoacetate, 3-ureidopropionic acid & indoxyl sulfate, or guanidinoacetate & indoxyl sulfate; or 3-ureidopropionic acid, guanidinoacetate & indoxyl sulfate) indicates the presence of a neurological autoimmune disease (e.g., MS) in the patient. As used herein, statistical significance refers to a p-value of less than 0.05, e.g., a p-value of less than 0.025 or a p-value of less than 0.01, using an appropriate measure of statistical significance, e.g., a one-tailed two sample t-test.

It would be appreciated by those in the art that the levels of the one or more biomarkers in the urine from a patient can be compared to a control in order to determine whether or not there is a decrease in the levels of one or more of the biomarkers in the patient. A control can be a sample from a control patient that does not suffer from a neurological autoimmune disease or from MS in which the level of the respective biomarker(s) is determined. Additionally or alternatively, a control can refer to a number or range of numbers that has been standardized to the level of the respective biomarker(s) in one or more control patients or a control population.

The methods described herein also can be used to determine whether or not a compound is effective for treating a subject having a neurological autoimmune disease. For example, urine can be collected at least one time before (e.g., a first urine sample) and at least one time after (e.g., a second urine sample) a compound is administered to a subject. A change in the level of a biomarker refers to the difference between the level of the biomarker in the second urine sample and the level of the biomarker in the first urine sample and can be expressed as the lack of a decrease in the level of the biomarker (e.g., an increase or no change in the level of the biomarker) or a decrease in the level of the biomarker.

In some embodiments, the subject being administered the compound is a human patient that is receiving a pharmaceutical composition (e.g., a drug), and the methods can be used to monitor and evaluate the response of the patient to the compound. For example, an increase in the level of any of the biomarkers identified herein in the second urine sample over the first urine sample is an indication that the compound is effective for treating a neurological autoimmune disease such as MS. On the other hand, a decrease in the level of any of the biomarkers identified herein in the second urine sample over the first urine sample is an indication that the compound is not effective for treating a neurological autoimmune disease such as MS.

In some embodiments, the subject being administered the compound can be a non-human animal (e.g., an animal model, e.g., an EAE animal or a NOD mouse). A subject can be administered a compound (e.g., a test compound) and the level of one or more of the biomarkers described herein can be determined. These methods can be used, for example, to screen compounds for their effectiveness in treating a subject having a neurological autoimmune disease. As indicated above, the lack of a decrease in the level of any of the biomarkers identified herein in the second urine sample over the first urine sample is an indication that the compound may be effective for treating a neurological autoimmune disease (e.g., MS), while a decrease in the level of any of the biomarkers identified herein in the second urine sample over the first urine sample is an indication that the compound likely is not effective for treating a neurological autoimmune disease (e.g., MS).

Compounds (e.g., test compounds) include, without limitation, nucleic acids (e.g., oligonucleotides), polypeptides (e.g., enzymes, antibodies), chemical compounds, extracts from bacteria, plant, fungi or animal cells, or mixtures thereof. Such compounds can be administered to a subject using any known means including, but not limited to, orally, intravenously, intramuscularly, intraperitoneally, subcutaneously, intradermally, or topically.

As used herein, a compound that is effective for "treating" a patient or a subject refers to a compound that manages, alleviates, ameliorates or remediates one or more symptoms associated with a neurological autoimmune disease. The symptoms associated with neurological autoimmune diseases are vast and include, simply by way of example, blurred or loss of vision, loss of coordination, loss of balance, loss of bladder control, sexual dysfunction, fatigue, fever, numbness, tingling and/or weakness of extremities, joint and/or muscle aches, weight loss, hair loss, skin rash, and combinations thereof.

Methods of collecting or expressing urine samples from human patients or from animal subjects are well known in the art, as are methods of handling and storing urine samples.

The biomarkers described herein can be detected in urine using any number of methods. For example, immunoassays are well known in the art and include, without limitation, enzyme-linked immunosorbent assays (ELISAs), radioimmunoassays, surround optical fiber immunoassay (SOFIA), cloned enzyme donor immunoassay (CEDIA), or magnetic immunoassay (MIA). The biomarkers described herein also can be detected using, for example, liquid-chromatography-mass spectrometry (LC-MS); gas-chromatography-mass spectrometry (GC-MS), liquid-chromatography-electrochemistry array metabolomics platforms (LCECA), fourier transform infrared spectroscopy (FTIR), capillary electrophoresis electrospray ionization mass spectrometry (CE-ESI-MS), and ultra-performance liquid chromatography mass spectrometry (UPLC-MS). In addition and as described herein, the biomarkers can be detected in urine using NMR (e.g., 1-dimensional (1D) or 2-dimensional (2D) NMR).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A: Preliminary Experiments and Results

Example 1

Sample Preparation

Groups of 5-to 6-week old female C57B1/6 mice were immunized with or without MOG 35-55 (MEVGWYRSPFS-RVVHLYRNGK (SEQ ID NO:1)) in complete Freund's adjuvant (CFA; 200 µg/mouse) subcutaneously as described (n=13 each) (Miller et al., 2007, *Curr. Protoc. Immunol.*, Ch 15, Unit 15 11; Mendel et al., 1995, *Eur. J. Immunol.*, 25:1951-9). The animals were monitored for clinical signs of EAE and scored until termination, which occurred on day 30 post-immunization (Miller et al., supra; Mendel et al., supra). Urine samples were collected daily starting day −1 until day 30 from controls and mice with EAE showing bilateral hind limb paralysis (scored 4). Three sample pools of 500 µl were prepared for each group of mice and the volumes were brought up to 600 µl by adding 100 µl deuterium oxide (pH of 7.2) prior to NMR analysis.

Example 2

Sample Analysis

NMR experiments were conducted on urine samples collected from controls and EAE mice using Bruker AVANCE DRX 500 MHz spectrometer equipped with 5 mm Triple-resonance Cryoprobe ($^1$H, $^{13}$C, $^{15}$N) with a Z-axis gradient. The 2D $^1$H-$^{13}$C HSQC NMR data was collected using the following parameters: 512 scans, 32 dummy scan, 1.5 s relaxation delay and with 64 fid size. All the spectra were processed using NMRPipe (see, for example, spin.niddk.nih-.gov/NMRPipe/) and peak matching, and peak assignments were performed using NMRViewJ Version 8.0 (see, for example, the World Wide Web at onemoonscientific.com/nmrview/summary.html) and chemical shift references from the Human Metabolomics Database (HMDB) (see, for example, hmdb.ca on the World Wide Web). The urinary metabolites that are differentially excreted in controls and EAE mice were noted and the metabolic intensities obtained in EAE mice were subtracted from those of control mice to determine fold-change for each metabolite. The data are presented in FIGS. 1 and 1A-1F.

Figure 1A:
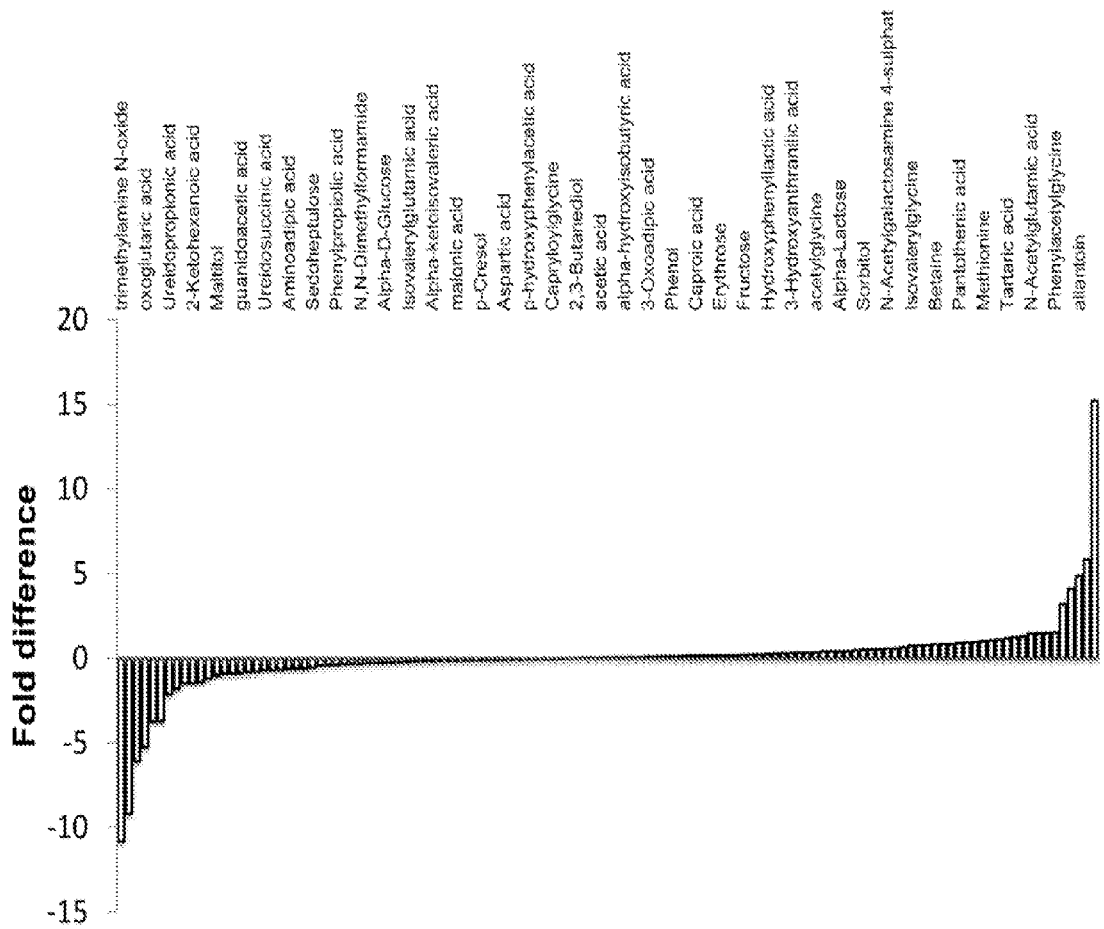
FIG. 1A shows the urine metabolites that are upregulated/downregulated in EAE mice. EAE was induced in C57Bl/6 mice using MOG 35-55 in CFA and urine samples were obtained from EAE mice that scored 3 to 4 and age-matched healthy mice on day 17 post-immunization. The samples were subjected to 2D 1H-13C HSQC NMR spectroscopy analysis and the data were analyzed to compare the composition of metabolites in EAE versus the control as described herein. The urine metabolites are represented on the x-axis and the fold difference on the y-axis. The metabolites with a positive difference are those that have a greater presence in EAE mice, and the metabolites with a negative difference are those that have a greater presence in control mice.
Figure 1B:
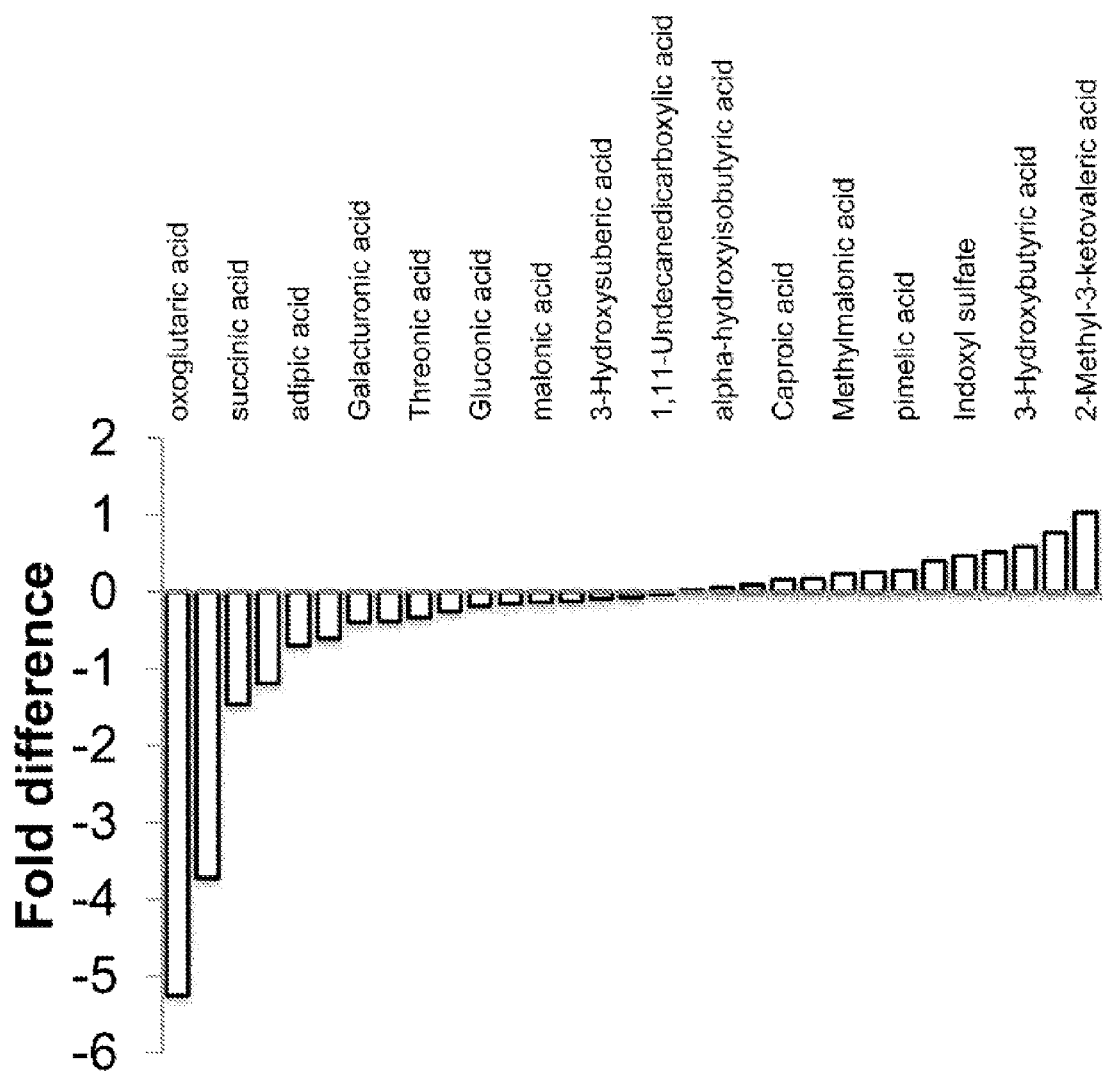
FIGS. 1(B)-(G) are graphs showing the overall results broken down by organic acids (FIG. 1B), amino acids (FIG. 1C), carbohydrates (FIG. 1D), microbial products (FIG. 1E), amines (FIG. 1F), and alcohols, ketones and aldehydes (FIG. 1G).
Figure 1C:
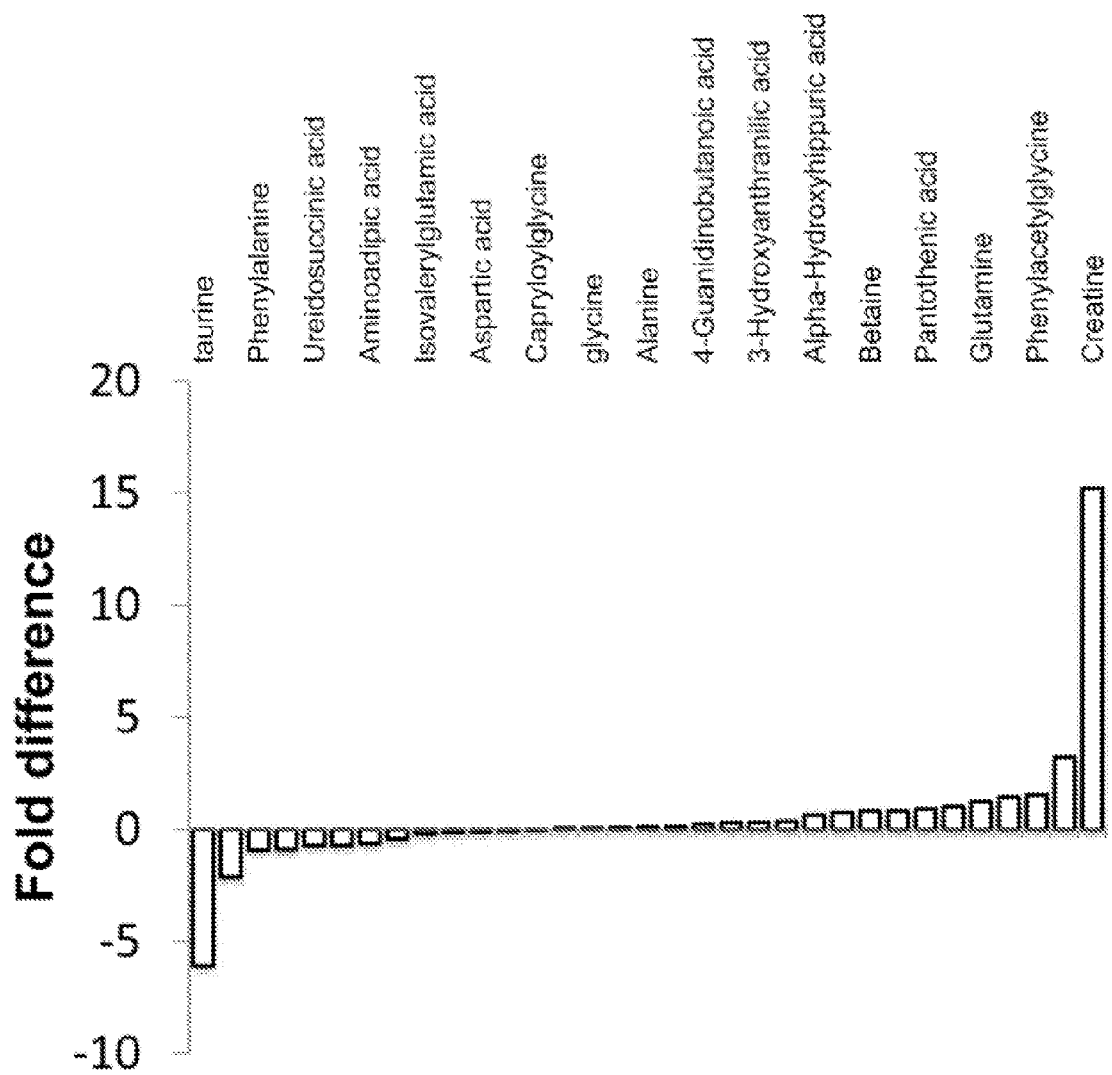
Figure 1D:
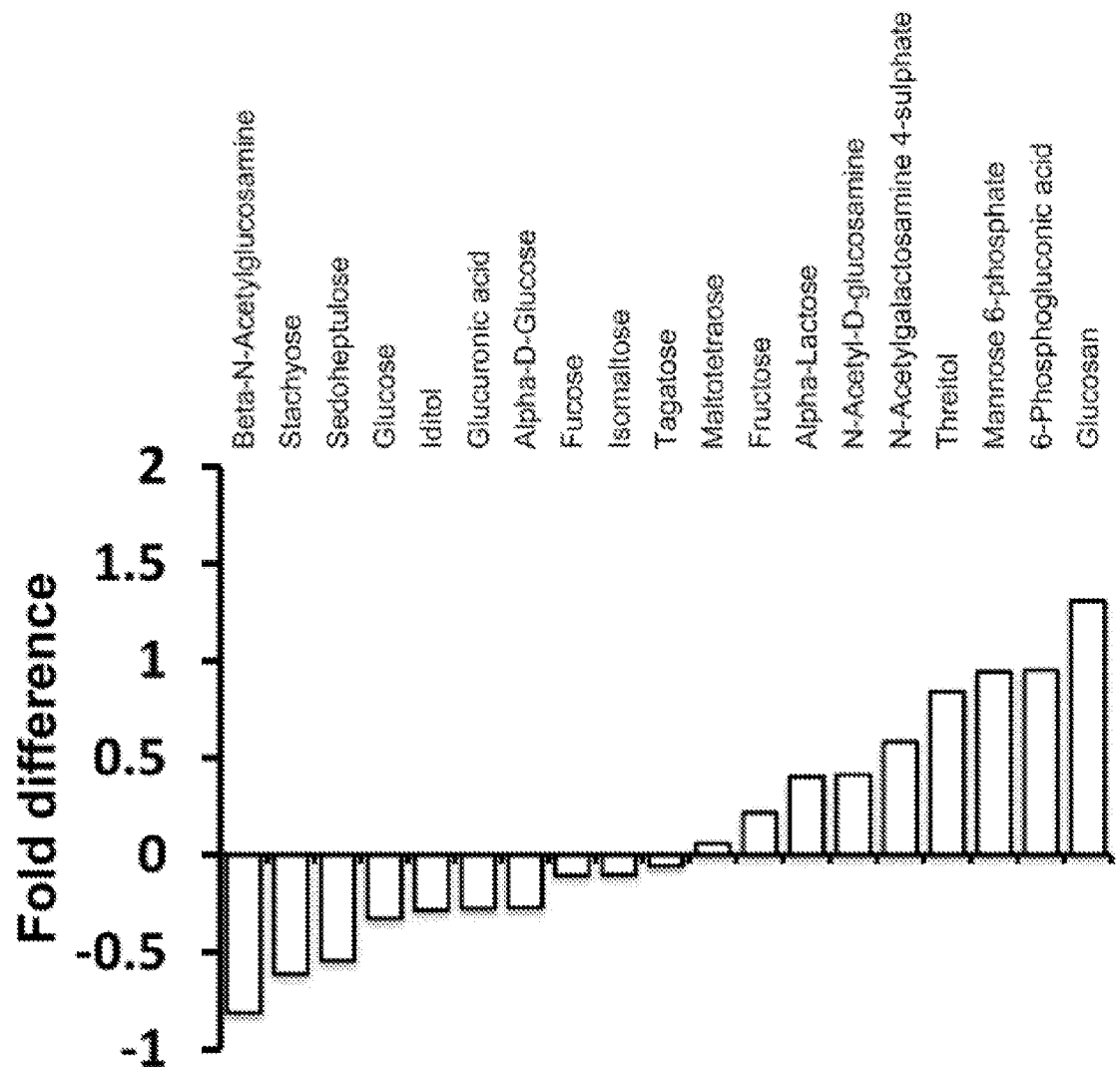
Figure 1E:
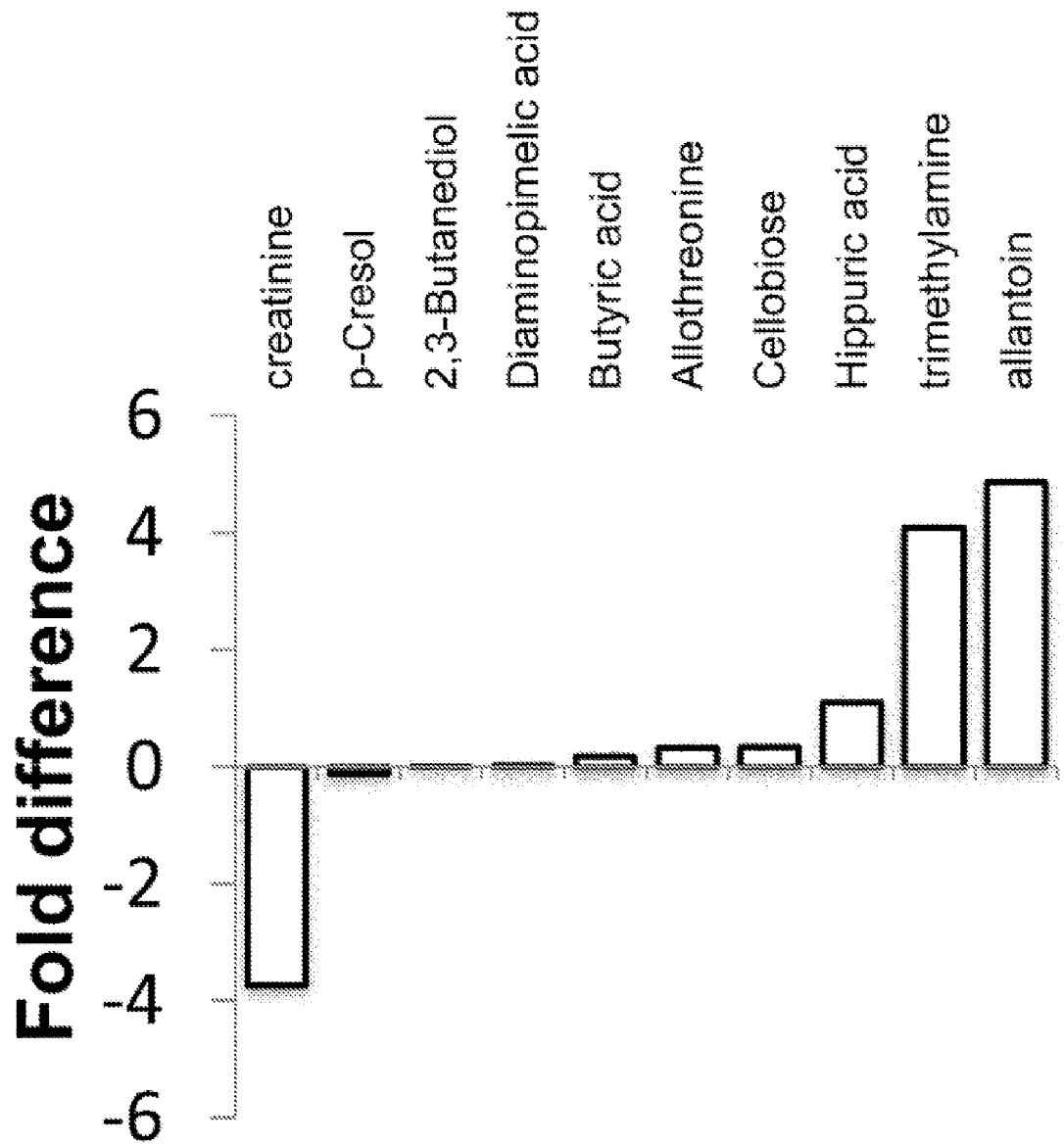
Figure 1F:
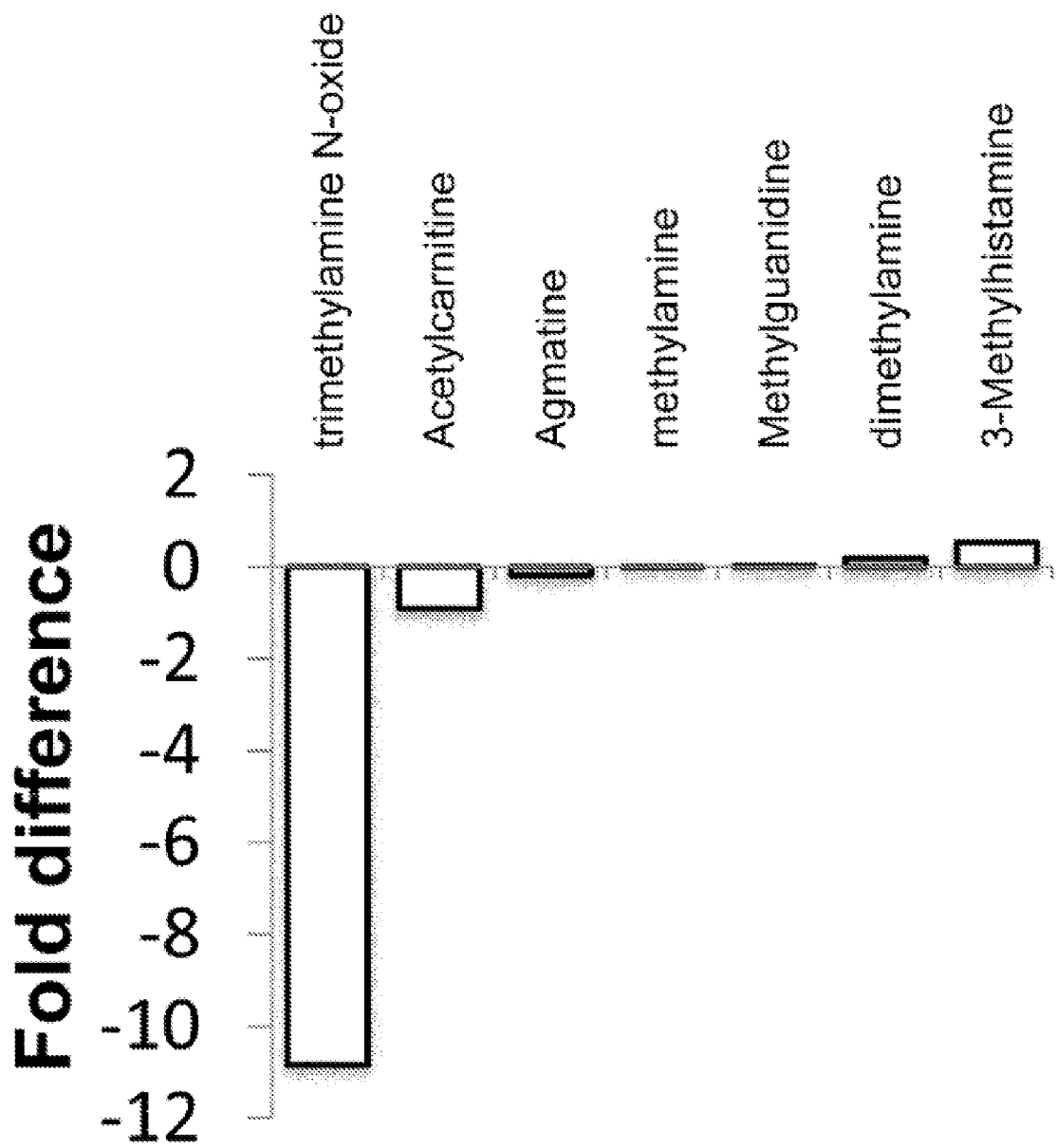
Figure 1G:
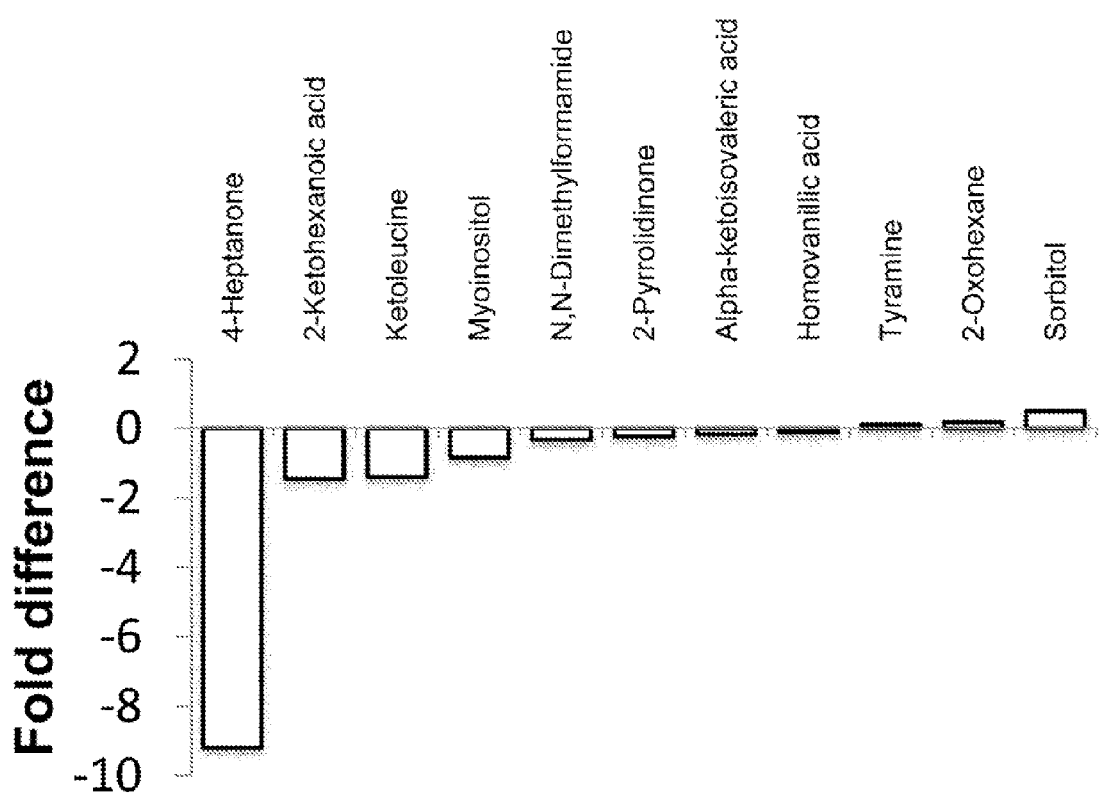
Figure 2:
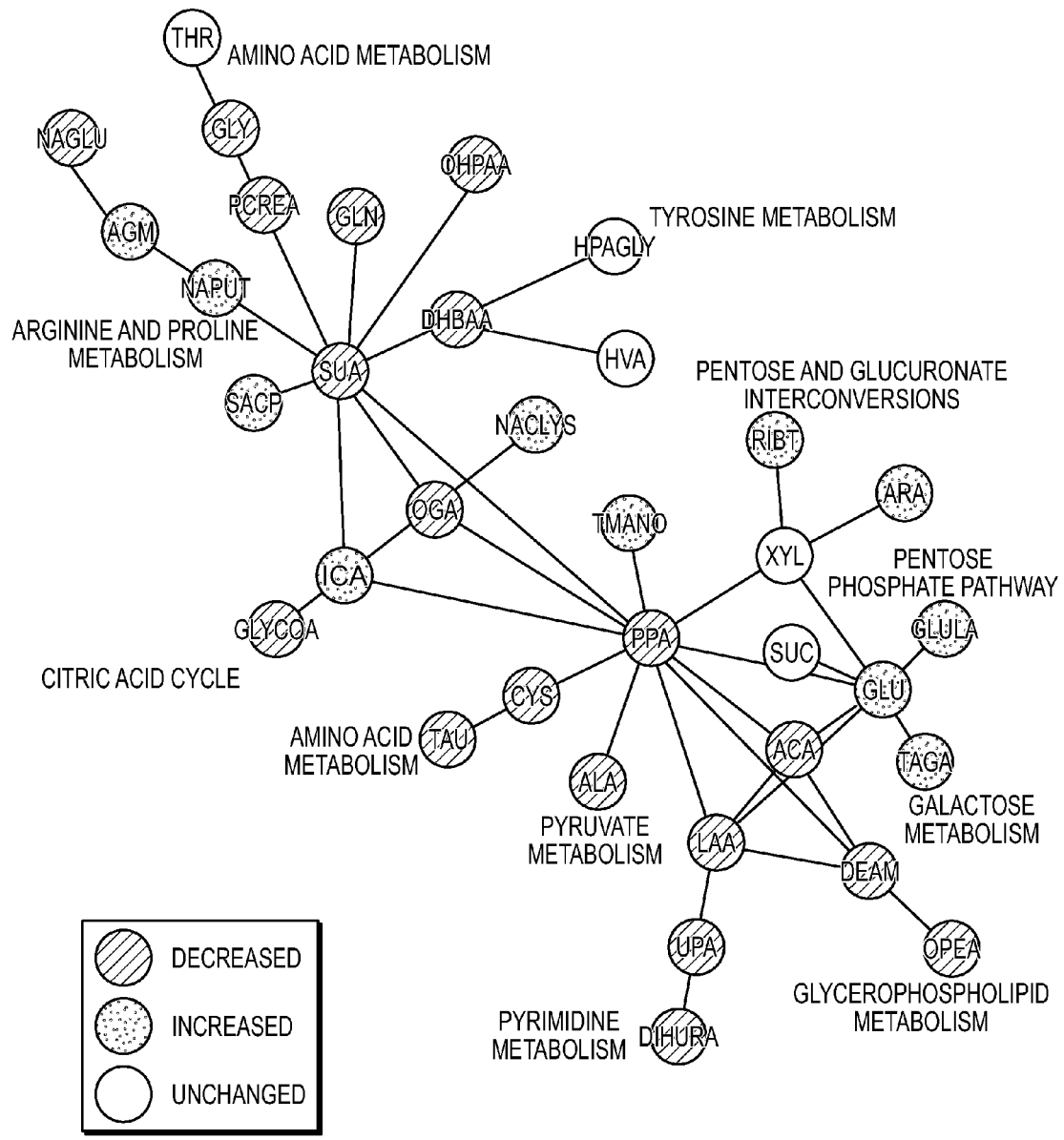
FIG. 2 is a schematic showing the metabolite pathway network developed from the results shown in FIG. 1.

FIG. 2 shows the pathway information for each of the urinary metabolites that are differentially excreted in EAE mice, which were obtained from the Kyoto Encyclopedia of Genes and Genomes (KEGG) (see, for example, genome.jp/keg/kegg3a.html on the World Wide Web) and BioCyc (see for example, biocyc.org on the World Wide Web). The urinary metabolites were linked with the nearest possible metabolite in the pathway.

Example 3

Summary of Preliminary Experiments and Results

The preliminary experiments above served to optimize the conditions for determining metabolites in urine. The preliminary results suggest that urine metabolites can be used to predict disease progression in CNS autoimmune diseases. In addition, the urine metabolites can be used to evaluate the efficacy of one or more drugs.

Part B: NMR Metabolomics-Based Analysis of Urine

Example 4

Mice

Six to eight-week-old female C57B1/6 (H-$2^b$) mice were obtained from the Jackson Laboratory (Bar Harbor, Me.). The mice were maintained in accordance with the animal protocol guidelines of the University of Nebraska-Lincoln, Lincoln, Nebr.

Example 5

Peptide Synthesis and Immunization Procedures

MOG 35-55 peptide (SEQ ID NO:1) was synthesized on 9-fluorenylmethyloxy-carbonyl chemistry (Neopeptide, Cambridge, Mass.) to a purity of more than 90% as verified by HPLC and mass spectroscopy. The peptide was dissolved in 1 ×PBS, and stored at −20° C. until use.

Example 6

Immunization and Treatment Procedures

The experimental design consisted of seven treatment groups (n=13). These include control, saline, complete Freund's adjuvant (CFA) alone, EAE treatment (see below), saline plus drug (Fingolimod), CFA plus drug, and EAE plus drug. Each treatment group was divided into three batches, each containing 4, 4 and 5 animals, respectively.

EAE treatment refers to the process of inducing experimental autoimmune encephalomyelitis (EAE) in mice, which is a MS-like disease characterized by inflammation and demyelination of the CNS. To induce EAE, peptide emulsions were prepared by mixing MOG 35-55 (SEQ ID NO:1) in CFA containing *Mycobacterium tuberculosis* H37RA extract (Difco Laboratories, Detroit, Mich.) to a final concentration of 5 mg/ml. Each animal received 200 μg of peptide-emulsion subcutaneously in the inguinal and sternal regions. In addition, Pertussis toxin (List Biological Laboratories, Campbell, Calif.) was administered (200 ng per mouse) intraperitoneally on day 0 and day 2 post immunization (Massilamany et al., 2010, *J. Neuroimmunol.*, 219:17-24; Massilamany et al., 2011, *J. Neuroimmunol.*, 230:95-104; Massilamany et al., 2011, BMC *Immunol.*, 12:40). Seven days post-immunization or in the no-injection control, fingolimod was dissolved in normal saline to a working dilution of 0.2 mg/ml, and administered intraperitoneally into the animals corresponding to drug-treated groups as indicated above at 1 mg/kg body weight daily until day 30.

Example 7

Urine Collection

Urine samples were collected both prior to and after disease induction. The urine collections occurred three times daily from each animal by expressing the bladder. The samples collected from each batch of animals were pooled on a daily basis and preserved at −80° C. until further analysis. In addition, the samples collected from individual animals on days 16, 23 and 30 post-immunization were preserved as separate aliquots.

Example 8

NMR Sample Preparation

For the 2D $^1$H-$^{13}$C HSQC experiments, 100 μL of a 50 mM phosphate buffer in 99.8% $D_2O$ (Isotec) at pH 7.2 (PBS, uncorrected) were added to each 500 μL urine sample to a final volume of 600 μL. For the 1D $^1$H NMR experiments, 600 μL of PBS was added to 10 μL of urine.

Example 9

NMR Data Collection and Analysis

NMR experiments were conducted with Bruker AVANCE DRX 500 MHz spectrometer equipped with 5 mm Triple-resonance Cryoprobe ($^1$H, $^{13}$C, $^{15}$N) with a Z-axis gradient. A BACS-120 sample changer with Bruker Icon software was used to automate the NMR data collection. The 1D $^1$H NMR data was collected at 298K with 32K data points, a spectrum width of 5483 Hz 128 scan and 16 dummy scans using an excitation sculpting pulse sequence. The 2D $^1$H-$^{13}$C HSQC NMR data was collected at 298K with 512 scans, 32 dummy scan and a 1.5 s relaxation delay. The spectrum was collected with 2048K data points and a spectrum width of 4734 Hz in the direct dimension and 64 data points and a spectrum width of 18864 Hz in the indirect dimension.

1D $^1$H NMR spectra were processed with the ACD/1D NMR manager version 12.0 (Advanced Chemistry Development, Inc.). After the residual water peaks were removed, intelligent binning was used to integrate each region with a bucket size of 0.025 ppm. The noise regions were removed by changing the value of the bins to zero. Each NMR spectrum was mean-centered and auto-scaled by the standard deviation (Zhang et al., 2011, *J. Proteome Res.*, 10:3743-54). Principal component analysis (PCA), Orthogonal Partial List Square Discreet Analysis (OPLS-DA) and S-plot were generated using SIMCA P+12 (UMETRICS). The PCA2Tree software was used to make the tree diagram (Werth et al., 2010, *Analytical Biochem.*, 399:56-63).

The 2D $^1$H-$^{13}$C HSQC spectra were processed using NMRPipe. Peak picking and peak matching were performed using NMR ViewJ Version 8.0. Peak intensities were normalized for each 2D NMR spectrum by dividing by the average peak intensity for a given spectrum. Each peak for each metabolite from each specific triplicate data set was further normalized by the maximum intensity of the metabolite and scaled to 100. The metabolite percent change was calculated relative to the EAE group. Chemical shift references from the Human Metabolomics Database were used to assign each NMR peak to a metabolite (Wishart et al., 2009, *Nuc. Acids Res.*, 37:D603-10).

Example 10

Experimental Results

Evidence is presented that the NMR spectrum of urinary metabolites can be used to diagnose MS by differentiating between healthy mice, EAE-mice, and EAE-mice treated with fingolimod, a drug recently approved for MS therapy.

Urine metabolites were evaluated by NMR spectroscopy using an experimental design that consisted of seven treatment groups: control, saline, complete Freund's adjuvant (CFA), EAE, saline plus fingolimod, CFA plus fingolimod and EAE plus fingolimod. FIG. 3 shows the one-dimensional (1D) $^1$H NMR spectra of urine obtained from healthy mice, EAE-mice, and EAE-mice treated with fingolimod. A set of NMR peaks (labeled B) are significantly increased in the spectra for healthy mice relative to diseased mice. Conversely, two sets of NMR peaks (labeled A and A') are increased in the diseased mice spectrum relative to healthy mice. These spectral differences correspond to a set of metabolites that are differentially up-regulated and down-regulated in EAE-mice and are potential biomarkers for MS. Additionally, the NMR spectra for the other control groups, saline, saline plus fingolimod or CFA plus fingolimod, were essentially identical to the NMR spectra for the healthy mice.

It was next evaluated whether fingolimod would alter the metabolomic profile of EAE-mice, consistent with its predicted efficacy against MS. As expected, the urine metabolites observed in the NMR spectra for the EAE mice treated with fingolimod resembled the NMR spectra for the healthy mice (FIG. 3). The spectral region B suppressed in EAE mice has increased in intensity (labeled B'). Similarly, the spectral regions A and A' have disappeared in EAE-mice treated with fingolimod, shifting the metabolomics profiles towards the healthy mice. To further quantitate the differences in the metabolites obtained in healthy and EAE-mice, multivariate statistical analysis techniques were used. A 2D plot from an orthogonal partial least square discrete analysis (OPLS-DA) revealed distinct clusters between the two groups (FIG. 4A). As expected, control mice injected with saline, CFA and fingolimod clustered together with the healthy mice. Notably, the EAE mice treated with fingolimod were also clustered with the controls. These results were further corroborated by generating a metabolomics tree diagram (FIG. 4B). The high boot-strap numbers (>50) indicate the statistical relevance of each cluster or node.

An S-plot from the OPLS-DA is shown in FIG. 5. Each point in the S-plot corresponds to a chemical shift range of 0.025 ppm or, more relevant, to a specific metabolite. The point (metabolite) that significantly contributes to the class cluster separation in the 2D scores plot are found at the extremes (labeled) of the S-plot. The S-plot and NMR spectra were compared to verify the spectral contributions to the class separation between healthy and EAE mice. Points in the S-plot represented by triangles (▲) were found to correlate with NMR peaks in the previously identified A, A' B and B' spectral regions in FIG. 3. These analyses validate the use of NMR spectroscopy technology to assess urine metabolites as indicators of disease progression in the EAE model.

Urinary metabolites were further analyzed using 2D $^1$H-$^{13}$C HSQC spectra obtained from urine samples pooled from a group of healthy or EAE mice. The use of pooled samples was necessary because of the low natural abundance of $^{13}$C-labeled metabolites. The 2D $^1$H-$^{13}$C HSQC spectra were compared between the two groups to identify the differences in peak intensities. The NMR peaks were then assigned to metabolites using Human Metabolomic Databases (hmdb.ca on the World Wide Web). Metabolites are assigned based on minimizing the chemical shift differences between the experimental values reported herein and the values deposited in the database, and maximizing the number of matching chemical shifts. The identity of the metabolites that were up- or down-regulated in EAE-relative to healthy mice were plotted (FIG. 6). The analysis revealed that 3-ureidopropionic acid (UDPA), guanidinoacetate (GA) and indoxyl sulfate (ISU) were significantly down-regulated in the EAE mice, thereby suggesting that any of these three metabolites can be used as markers of a neurological autoimmune disorder.

Metformin, a drug used for diabetes mellitus, has been shown to attenuate EAE progression in animal models (Nath et al., 2009, *J. Immunol.*, 182:8005-14). It was noted that a NMR peak (UN_2 in FIG. 6) appears to have a structure similar to metformin. It was postulated, therefore, that a metformin-like metabolite might play a role in MS. A second unknown aromatic metabolite also was observed, the concentration of which was relatively higher in EAE as compared to healthy mice (FIG. 6). The detection of these structurally uncharacterized metabolites provides new insights as to the novel pathways that might be involved in EAE/MS pathogenesis.

Example 11

Conclusions

It has been demonstrated herein that the metabolite composition of urine samples differs between healthy and EAE-mice. Several key metabolites also have been identified that are consistently down- or up-regulated in EAE-mice in comparison with controls.

In addition, the metabolites can be used in the evaluation of in vivo efficacy of potential drug-leads and designing patient-specific treatments.

The NMR analysis of urine by NMR takes approximately 10 minutes per sample and completely lacks any of the risks or side effects associated with the analysis of other biological samples, such as cerebrospinal fluid.

The lack of cure for MS and its increasing prevalence amoung the population of young adults further emphasizes the need to identify reliable markers of disease progression. Thus, the NMR analysis of urine samples to evaluate the metabolites identified herein holds the promise of being an easy, fast, and safe diagnostic tool for MS.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary.

Likewise, any subset or combination of these is also specifically contemplated and disclosed.

What is claimed is:

1. A method of monitoring the progression of EAE in a rodent comprising:
   collecting a urine sample from a rodent having EAE; and
   determining the levels of one or more biomarkers in the rodent's urine, wherein the one or more biomarkers compromise 3-ureidopropionic acid;
   wherein an increase in the level of the one or more biomarkers in the rodent's urine is indicative of the progression of EAE in the rodent.

2. The method of claim 1, wherein the one or more biomarkers further comprise guanidinoacetate.

3. The method of claim 1, wherein the one or more biomarkers further comprise indoxyl sulfate.

4. The method of claim 1, wherein the one or more biomarkers further comprise guanidinoacetate and indoxyl sulfate.

5. The method of claim 1, wherein the levels of the one or more biomarkers are determined using an immunoassay, chromatography, spectroscopy or NMR.

6. The method of claim 1, wherein the levels of the one or more biomarkers in the rodent's urine are compared to the levels of the one or more biomarkers in a control rodent that does not suffer from EAE.

7. The method of claim 1, wherein the levels of the one or more biomarkers in the rodent's urine are compared to a standardized control.

8. A method of determining whether a compound is effective for ameliorating the symptoms of EAE in a rodent, comprising:
   collecting a first urine sample from a rodent having EAE;
   determining the levels of one or more biomarkers in the first urine sample, wherein the one or more biomarkers comprise 3-ureidopropionic acid;
   administering a compound to the rodent having EAE;
   collecting a second urine sample from the rodent having EAE; and
   determining the levels of the one or more of the biomarkers in the second urine sample,
   wherein a decrease in the level of one or more biomarkers in the second urine sample relative to the first urine sample is indicative of a compound that is effective for ameliorating the symptoms of EAE in a rodent.

9. The method of claim 8, wherein the one or more biomarkers further comprise guanidinoacetate.

10. The method of claim 8, wherein the one or more biomarkers further comprise indoxyl sulfate.

11. The method of claim 8, wherein the one or more biomarkers further comprise guanidinoacetate and indoxyl sulfate.

12. The method of claim 8, wherein the levels of the one or more biomarkers are determined using an immunoassay, chromatography, spectroscopy or NMR.

* * * * *

UNITED STATES PATENT AND TRADEMARK OFFICE
CERTIFICATE OF CORRECTION

PATENT NO. : 9,304,123 B2
APPLICATION NO. : 13/962571
DATED : April 5, 2016
INVENTOR(S) : Robert Powers et al.

Page 1 of 1

It is certified that error appears in the above-identified patent and that said Letters Patent is hereby corrected as shown below:

On the title page,

Item (56), Column 1; Line 9 (Publications): Delete "Neourscience" and insert -- Neuroscience --, therefor.

In the claims,

Column 11; Line 5: In Claim 1, delete "rodent" and insert -- rodent, --, therefor.

Column 11; Line 9: In Claim 1, delete "compromise" and insert -- comprise --, therefor.

Column 12; Line 14: In Claim 8, after "of" insert -- the --.

Signed and Sealed this
Twenty-eighth Day of June, 2016

Michelle K. Lee
*Director of the United States Patent and Trademark Office*